(12) United States Patent
Boisivon et al.

(10) Patent No.: US 8,119,817 B2
(45) Date of Patent: Feb. 21, 2012

(54) PROCESS FOR SEPARATING THE DIASTEREOMERS OF RSS-AND SSS-N-α[1-CARBOXY-3-PHENYLPROPYL]LYSYLPROLINE

(75) Inventors: Frédéric Boisivon, Aubigny aux Kaisnes (FR); Jean Debas, Eppeville (FR); Gérard Richet, St. Quentin (FR)

(73) Assignee: Degussa-Huels AG, Frankfurt am Main (DE)

( * ) Notice: Subject to any disclaimer, the term of this patent is extended or adjusted under 35 U.S.C. 154(b) by 0 days.

(21) Appl. No.: 12/589,621

(22) Filed: Aug. 3, 1999

(65) Prior Publication Data

US 2011/0077412 A1    Mar. 31, 2011

Related U.S. Application Data

(60) Provisional application No. 60/133,533, filed on May 10, 1999.

(51) Int. Cl.
C07D 207/16 (2006.01)
A61K 31/401 (2006.01)
A61K 31/40 (2006.01)

(52) U.S. Cl. ........................ 548/533; 514/423

(58) Field of Classification Search ............ 548/533; 514/423

See application file for complete search history.

(56) References Cited

U.S. PATENT DOCUMENTS 4,374,829 A * 2/1983 Harris et al. .................. 514/15.7
4,472,380 A * 9/1984 Harris et al. .................. 514/15.7

OTHER PUBLICATIONS

Qin et al., Journal of Liquid Chromatography 1993, 16(17), 3713-3734.*
Blacklock et al., J. Org. Chem. 1988, 53, 836-844.*

* cited by examiner

Primary Examiner — Jason M Nolan
(74) Attorney, Agent, or Firm — Smith, Gambrell & Russell, LLP

(57) ABSTRACT

A process for separating the diastereomers of RSS— and SSS—N-α[1-carboxy-3-phenylpropyl]lysylproline is described. Previous chromatographic processes for separating the diastereomers of this peptide active substance, such as for example adsorption chromatography, exhibited disadvantages with regard to the solvents used and throughput. These disadvantages do not occur if basic ion exchangers are used in the chromatographic separation of the diastereomers. In particular, purely aqueous solutions may be used as the eluent.

14 Claims, No Drawings

PROCESS FOR SEPARATING THE DIASTEREOMERS OF RSS-AND SSS-N- α [1-CARBOXY-3-PHENYLPROPYL] LYSYLPROLINE

REFERENCE TO A RELATED APPLICATION

The present application claims the benefit of provisional application 60/133,533, filed May 10, 1999 which is incorporated herein by reference.

INTRODUCTION AND BACKGROUND

The present invention relates to a process for the chromatographic separation of mixtures of diastereomers comprising RSS— and SSS—N-α[1-carboxy-3-phenylpropyl]lysylproline (Lisinopril®; also denoted LP below).

Lisinopril® is an ACE inhibitor and is licensed as an antihypertensive.

When this peptide derivative is synthesized from two chiral amino acids, a new chiral center is formed (J. Org. Chem. 1988, 53, 836 et seq.). However, the reaction used does not proceed completely selectively with regard to this center. As a consequence, two diastereomers are inevitably formed, only one of which constitutes the actual active substance.

U.S. Pat. No. 4,472,380 and U.S. Pat. No. 4,374,829 describe the separation of the diastereomers thereof by adsorption chromatography on XAD-2 phases. The eluent used is a mixture comprising an aqueous ammonia solution and an organic solvent, such as for example methanol or acetonitrile.

The disadvantages of this chromatographic process are firstly that, when purifying the reaction solution from an LP production process, this operation is dependent upon the presence of organic solvents in the eluent as the compounds to be separated would otherwise either not be eluted from the stationary phases or would be eluted in an inadequately purified form. Residues of all kinds in the actual active substance and in particular these organic solvents are, however, highly undesirable, especially in the pharmaceuticals sector, as they could give rise to side effects or even be toxic. Reference may be made in this connection to the necessity of complying with the specification of the active substance required by government regulations.

Furthermore, addition of the organic solvents is a cost factor in the industrial production process with regard to use and recycling. Moreover, the stated adsorption chromatography columns have poor loadability for this separation task, meaning that throughput, viewed on an industrial scale, leaves something to be desired.

Accordingly, it is an object of the invention to separate the diastereomers of RSS— and SSS—N-α[1-carboxy-3-phenylpropyl]lysylproline, without encountering the disadvantages of the prior art chromatographic processes, which may in particular be performed without addition of organic solvents during separation, in particular during purification of the reaction solution from an LP production process, and which permits the stationary phase to be extremely highly loaded with the mixture of substances to be purified.

SUMMARY OF THE INVENTION

The above and other objects which are not stated in greater detail can be advantageously achieved by a separation method which employs basic ion exchangers, without resorting to use of organic solvents.

Completely unexpectedly, by using chromatographic means comprising basic ion exchangers for separating the diastereomers of RSS— and SSS—N-α[1-carboxy-3-phenylpropyl]lysylproline, the separated diastereomers are obtained in a manner superior to that of the chromatographic processes of the prior art. In particular, it is possible to dispense completely with the use of organic cosolvents.

Any ion exchangers known to the person skilled in the art may be used, provided that they have basic resins on the resin surface thereof. It is advantageous to use chromatographic means which comprise weakly basic ion exchangers. Weakly basic ion exchangers based on polyacrylate or polystyrene are preferably used. Very particularly preferred ion exchangers are A845 or A847 (Purolite Company), IRA67 (Rohm&Haas), Diaion WA10 or 11 (Mitsubishi Chemical) as well as MP62 or MP64 (Bayer AG). These materials are well known in the art.

A purely aqueous solution containing added acidic or basic constituents may be used as the eluent for separating the diastereomers. Aqueous acidic solutions, for example hydrochloric acid or sulfuric acid, or aqueous basic solutions, for example containing ammonia or sodium hydroxide, are preferably taken into consideration.

DETAILED DESCRIPTION OF INVENTION

One particular feature of the ion exchangers used according to the invention is that very good separation of the diastereomer mixtures is achieved even if the ion exchange columns are overloaded. Overloading occurs when the quantity of the mixture introduced into the chromatographic means is so large that products leave the chromatographic means again before elution is begun. An upper limit for loading is determined by the economic viability of the separation and is in particular dependent upon the SSS content of the mixture. When loading is excessively high, the mixed fraction becomes too large in comparison with the pure fraction of the desired diastereomer which is obtained. The precise quantity must be determined individually for each resin. In relation to A845, this quantity is preferably such that less than 150 g, preferably less than 140 g, of diastereomer mixture are applied per litre of resin. In comparison with U.S. Pat. No. 4,472,380, which describes loadings of <1 g/l of resin, loadings of >100 g/l of resin may be achieved in the process according to the invention.

The process according to the invention for separating RSS and SSS—N-α[1-carboxy-3-phenylpropyl]lysylproline may be performed highly effectively on an industrial scale. Depending upon the separation conditions, it may happen that, in addition to the fractions containing pure diastereomers, certain fractions are rinsed from the column which may contain greater or lesser proportions of diastereomer mixtures. A preferred development of this invention comprises collecting these mixed fractions and adding them to the mixture to be separated in the next separation run, i.e. before further diastereomers are introduced into the column. It is, however, conceivable for the stated mixed fractions from individual separation runs to be collected and subsequently to be purified together in the chromatographic means. In this manner, it is possible to maximize the effectiveness of the method, as all the proportions of the desired SSS diastereomer may be obtained in pure form.

The process according to the invention yields aqueous solutions of acidic peptide derivatives of a purity such that the pure diastereomer may be isolated directly from the solution obtained. Isolation may be achieved by using any options obvious to the person skilled in the art, such as for example spray drying or preferably crystallization and drying. Before crystallization, the solution is optionally concentrated and/or clarified with activated carbon.

It is advantageous if the diastereomer mixture to be separated is deionized before introduction into the ion exchange columns. Deionization may also be performed by ion exchange chromatography. One example is illustrated in J. Org. Chem. 1988, 53, 836 et seq. which disclosure is relied on and incorporated herein by reference.

It is also advantageous if the diastereomer mixture to be separated is decolorized before introduction into the ion exchange columns, so that isolation may be performed immediately after separation of the diastereomers without having to take account of colored constituents originating from synthesis of the active substance, which could possibly modify the color of the product.

This may be achieved by methods familiar to the person skilled in the art, for example by clarification with activated carbon. A chromatographic method is, however, preferred in this case too, in which the solution containing diastereomers is purified first on a basic resin and then on an acidic resin. Since the colored impurities are frequently present in the solution in very small quantities, the columns may be severely overloaded using this method without any negative impact on the effectiveness of decolorizing. Loading is determined by the particular individual case. Preferably, however, ratios of 510 mol of substance per liter of basic resin % and 10-20 mol of substance per liter of acidic resin are established.

It is accordingly possible according to the invention to convert a solution originating from an industrial production process and comprising a mixture of—and COO-protected RSS— and SSS—N-α[1-carboxy-3-phenylpropyl]lysylproline, after deprotection, deionization and optionally decolorizing, into the pure active substance SSS—N-α[1-carboxy-3-phenylpropyl]lysylproline in a manner which is extremely advantageous for an industrial process.

The presence of basic ion exchangers in the chromatographic means is of vital significance to the success of the present invention. The stated means may, inter alia, comprise arrangements in which combinations of two or more optionally different chromatographic means are present (for example coupled with adsorption chromatography). Such means are within the scope of the invention if at least one of these means comprises basic ion exchangers.

An apparatus for the chromatographic purification of substances, for example a chromatography column, may be taken to comprise a means for the purposes of the invention.

Examples

An LP product solution is produced in a similar manner to the process described in J. Org. Chem. 1988, 53, 836 et seq. After deionization, the solution is decolorized by chromatography on a weakly basic acrylic resin (A845). Water is used as the mobile solvent. Loading is 4 kg of diastereomer mixture/liter of resin. The solution is then pumped over a weakly acidic resin (C105 from Purolite Company). The loading in this case is 2 kg of diastereomer mixture/liter of resin. The solvent used is again water. A clear solution is obtained (transmission 9697% at a conc. of 50 g of LP/liter of solution). The diastereomer yield is 94% relative to the deionized solution at a purity of >98 area % according to HPLC.

The resultant solution is purified using 0.9 N hydrochloric acid on the weakly basic ion exchanger (A845, flow rate: 0.5 bed volume/h, room temperature). Loading is 100-130 g of diastereomer mixture per 1 liter of resin. A pure SSS isomer fraction is obtained at 75% yield, calculated relative to the quantity of SSS diastereomer introduced before the separation. The subsequently obtained mixed fraction (23% of the overall quantity of diastereomers) is collected and may be recycled.

The resultant solution of the pure SSS isomer is adjusted to pH 5-5.6 and optionally again clarified with activated carbon and microfiltered before being concentrated. Once crystallization is complete, the mixture is filtered and the product washed with distilled water. The filter cake is then dried. Crystalline SSS—N-α[1-carboxy-3-phenylpropyl]-lysylproline is obtained in two crystallisation stages at 90% crystallization yield. Comparable results can be obtained by employing other basic ion exchangers.

Further variations and modifications of the foregoing will be apparent to those skilled in the art and are intended to be encompassed by the claims appended hereto.

Provisional application No. 60/133,533 filed May 10, 1999 is relied on and incorporated herein by reference.

The invention claimed is:

1. Process for separating diastereomers of RSS— and SSS—N-α[1-carboxy-3-phenylpropyl]lysylproline contained in a mixture thereof comprising contacting said mixture with a basic ion exchanger in the absence of organic solvents.

2. The process according to claim 1, wherein said ion exchanger is a weakly basic ion exchanger.

3. The process according to claim 1, further comprising employing acidic or basic purely aqueous solutions as an eluent.

4. The process according to claim 2, further comprising employing acidic or basic purely aqueous solutions as an eluent.

5. The process according to claim 1, further comprising overloading the ion exchanger with said mixture.

6. The process according to claim 2, further comprising overloading the ion exchanger with said mixture.

7. The process according to claim 3, further comprising overloading the ion exchanger with said mixture.

8. The process according to claim 1, further comprising collecting a mixed fraction of the diastereomers and adding said fraction to the mixture to be separated in a following separation run, or purifying the mixed fractions from individual separation runs together.

9. The process according to claim 2, further comprising collecting a mixed fraction of the diastereomers and adding said fraction to the mixture to be separated in a following separation run, or purifying the mixed fractions from individual separation runs together.

10. The process according to claim 3, further comprising collecting a mixed fraction of the diastereomers and adding said fraction to the mixture to be separated in a following separation run, or purifying the mixed fractions from individual separation runs together.

11. The process according to claim 4, further comprising collecting a mixed fraction of the diastereomers and adding said fraction to the mixture to be separated in a following separation run, or purifying the mixed fractions from individual separation runs together.

12. The process according to claim 1, wherein pure diastereomer is directly isolated from a resultant solution by crystallization.

13. The process according to claim 1, wherein the diastereomer mixture to be separated is deionized before separation.

14. The process according to claim 1, wherein the diastereomer mixture to be separated is decolorized before separation.

* * * * *